United States Patent [19]

Photis

[11] 4,234,508
[45] Nov. 18, 1980

[54] PROCESS FOR PREPARING CYANOHYDRIN ESTERS

[75] Inventor: James M. Photis, Ridgefield, Conn.

[73] Assignee: Stauffer Chemical Company, Westport, Conn.

[21] Appl. No.: 80,957

[22] Filed: Oct. 1, 1979

[51] Int. Cl.³ .............. C07C 121/38; C07C 121/46; C07C 121/75

[52] U.S. Cl. .............. 260/465 D; 260/464; 260/465.4

[58] Field of Search ............. 260/465 D, 464, 465.4

[56] References Cited

FOREIGN PATENT DOCUMENTS 52-142046  11/1977  Japan .

OTHER PUBLICATIONS

Cox et al., *Organic Synthesis Collective*, vol. 2, p. 7 (1943).
Wagner et al., *Organic Synthesis Collective*, vol. 3, p. 324 (1955).
Nasipuri et al., *J. Indian Chemical Soc.*, 44, p. 556 (1967).
Gassman et al., *Tetrahedron Letters*, pp. 3773–3776 (1978).
Umino et al., *Tetrahedron Letters*, No. 33, pp. 2875–2876 (1976).
Sugimoto et al., *J. Chem. Soc. Chem. Comm.*, pp. 926–927 (1978).
Kinishi et al., *Agric. Biol. Chem.*, 42 (4), pp. 869–872 (1978).
Borch et al., *J. Org. Chem.*, 37, pp. 726–729 (1972).

*Primary Examiner*—Dolph H. Torrence
*Attorney, Agent, or Firm*—William C. Gerstenzang

[57] ABSTRACT

Cyanohydrin esters are prepared by reacting a carboxylic acid anhydride represented by the formula

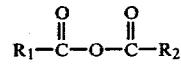

with an alkali metal cyanide and an alkali metal borohydride.

11 Claims, No Drawings

PROCESS FOR PREPARING CYANOHYDRIN ESTERS

BACKGROUND OF THE INVENTION

The present invention relates to a novel process for the preparation of cyanohydrin esters. More particularly, the present invention relates to the preparation of cyanohydrin esters directly from carboxylic acid anhydrides.

Cyanohydrin esters are important industrial materials both as intermediates to be used in making other compounds and as compounds having utility in and of themselves.

An example of the former is meta-phenoxybenzaldehyde cyanohydrin acetate, which is represented by the formula:

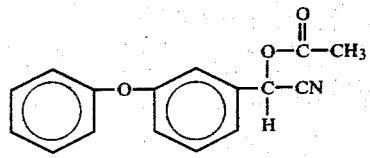

An example of the latter is the pyrethroidtype insecticide represented by the formula:

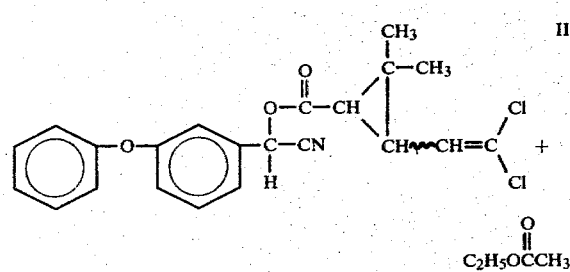

The compound of formula I can be used as an intermediate cyanohydrin ester from which the insecticidally-active cyanohydrin ester of formula II is prepared, as follows:

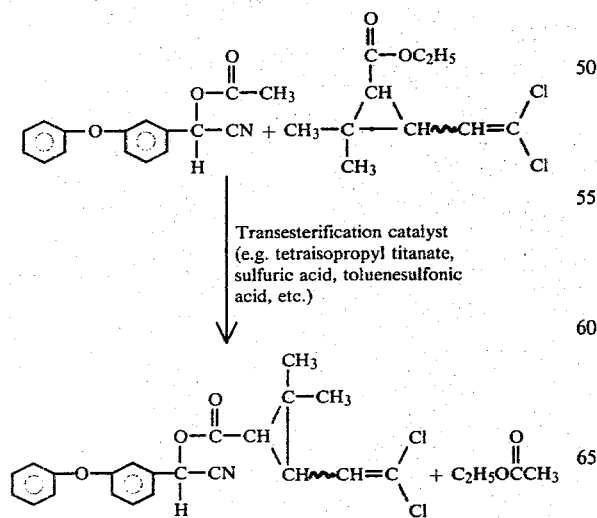

This method of preparing cyanohydrin esters of the type represented by compound II presupposes the availability of the intermediate compound I.

The intermediate cyanohydrin ester represented by formula I can be prepared by reacting a free cyanohydrin with acetic anhydride, as follows:

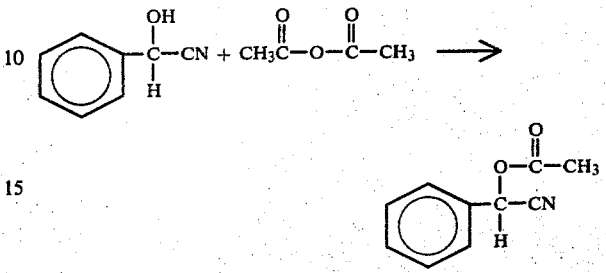

This overall method for preparing cyanohydrin esters of the type represented by formula II is not preferred for two reasons. The first is that it is a two-step process, the first step being the preparation of an intermediate cyanohydrin ester (compound I), and the second step being the further reaction of the intermediate to form the final product. The second objection is that it requires, in the first step, the handling of a free cyanohydrin. Free cyanohydrins are unstable compounds which can release HCN.

It is highly desirable therefore that a method be provided for preparing cyanohydrin esters by a one-step process which does not require the use of free cyanohydrins.

SUMMARY OF THE INVENTION

It is an object of the present invention to provide a novel one-step process by which cyanohydrin esters are prepared directly from carboxylic acid anhydrides.

It has now been discovered that cyanohydrin esters can be readily prepared directly from carboxylic acid anhydrides by reacting the carboxylic acid anhydrides with an alkali metal cyanide and an alkali metal borohydride.

In accordance with the present invention there is provided a process for the preparation of cyanohydrin esters represented by the formula

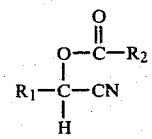

wherein $R_1$ and $R_2$ may be the same or different and each represents an alkyl, alkenyl, cycloalkyl, aryl, aralkyl, alkylphenyl, diphenyl ether, or polyphenyl radical, or a radical made up of any combination thereof; and may contain an inert substituent selected from the group consisting of halogen, alkyl and alkoxy; the radical having a total number of carbon atoms ranging from 1 to about 30; which comprises reacting a carboxylic acid anhydride represented by the structure

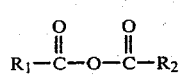

with an alkali metal cyanide and an alkali metal borohydride.

DETAILED DESCRIPTION OF THE INVENTION

In practicing the present invention a carboxylic acid anhydride is reacted with an alkali metal borohydride and alkali metal cyanide to form a cyanohydrin ester. The reaction is preferably conducted in an aqueous reaction media comprising water and a water miscible solvent or in a two-phase reaction media comprising water and a water immiscible solvent. When conducting the reaction in the aqueous media, no catalyst is required. When conducting the reaction in a two-phase reaction media it is preferred that a phase transfer catalyst be present.

The carboxylic acid anhydrides used in the practice of the present invention are represented by the formula:

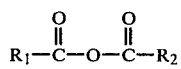

wherein $R_1$ and $R_2$ have the aforedescribed meanings, and include, but are not limited to benzoic anhydride, butyric anhydride, 4-chloro-α-isopropyl phenylacetic 3-phenoxybenzoic anhydride, 3-phenoxybenzoic chrysanthemic anhydride and 3-phenoxybenzoic dichlorochrysanthemic anhydride, although 3-phenoxybenzoic dichlorochrysanthemic anhydride is preferred.

The alkali metal cyanides which are used in the practice of the present invention include, but are not limited to sodium cyanide, potassium cyanide, and lithium cyanide. The preferred alkali metal cyanides are sodium cyanide and potassium cyanide, although sodium cyanide is most preferred. The amount of alkali metal cyanide used in the practice of the present invention is at least the stiochiometric equivalent of the total amount of carboxylic acid anhydride used. The amount of alkali metal cyanide used generally ranges from about 1 to about 3 or more equivalents of the carboxylic acid anhydride used, although preferably it ranges from about 1.05 to about 1.5 equivalents.

The alkali metal borohydrides used in the practice of the present invention include sodium borohydride, potassium borohydride, lithium borohydride and mixtures thereof; although sodium borohydride is preferred, because it is readily available.

About 0.25 equivalents of alkali metal borohydride are required to react with the carboxylic acid anhydride, since all four hydrogens on the alkali metal borohydride are active.

The amount of alkali metal borohydride present in the reaction mixture should not exceed about 0.5 equivalents, because amounts in excess of about 0.5 equivalents can result in the formation of alcohols rather than cyanohydrin esters.

When conducting the reaction in the aqueous media, a solution of the carboxylic acid anhydride in a water miscible solvent is prepared and this solution is then brought into contact with an aqueous solution of the alkali metal cyanide and alkali metal borohydride at a temperature and for a time sufficient to form the cyanohydrin esters.

The concentrations of the solution of carboxylic acid anhydride in the water miscible solvent ranges from about 25 grams of carboxylic acid per liter of solution to about 250 grams of carboxylic acid anhydride per liter of solution. Although lower concentrations may be used, they are not preferred because at low concentrations a hydrolysis of the anhydrides to carboxylic acids can occur to a significant degree.

Higher concentrations, although they may be used, are not preferred because at higher concentrations the reduction of the anhydrides to alcohols can become significant.

The water miscible solvents used in the practice of the present invention include, but are not limited to dioxane, tetrahydrofuran, dimethoxyethane, bis-(2-methoxyethyl) ether, bis-(2-ethoxyethyl) ether and other such polyether solvents, although dioxane is preferred.

The concentrations of alkali metal cyanide and alkali metal borohydride in the aqueous solution thereof range from about 50 to about 500 grams alkali metal cyanide per liter of solution and from about 5 to about 100 grams alkali metal borohydride per liter of solution. At higher concentrations direct reduction of the reactants to alcohols can result, while at lower concentrations reaction rate can be slow, the desired reaction can be incomplete and hydrolysis of the anhydrides to carboxylic acid can become appreciable.

The solution of carboxylic acid anhydride in water miscible solvent and the aqueous solution of alkali metal cyanide and alkali metal borohydride are each prepared by conventional means.

The two solutions are then brought into contact by mixing them together, in any order. This is to say, either solution may be added to the other. The addition of one solution to the other may be accomplished by either metering controlled amounts of each into a reaction zone on a continuous basis, or by simply pouring one into the other in batch mixing equipment.

Once the two solutions are brought together, the reaction will begin. No catalyst is required.

The reaction is mildly exothermic and external cooling may be required.

The reaction temperature should not be permitted to exceed about 50° C., and preferably should be maintained within the range of from about 20° to about 40° C. At temperatures in excess of about 50° C. hydrolysis of the anhydrides to carboxylic acids and direct reduction of the alkali metal cyanides to alcohols can take place to an appreciable degree, while at temperatures below about 20° C. reaction rate becomes relatively low, and this increases the likelihood of hydrolyzing the anhydrides to carboxylic acids.

The essential completion of the reaction will be indicated by the disappearance of the characteristic carbonyl absorption bands in the infrared spectrum.

The reaction can generally be essentially completed in time periods ranging from about 15 minutes to about 1 hour.

Once the reaction is completed, the product cyanohydrin ester can be recovered from the aqueous reaction mass by conventional means. A preferred conventional method for recovering the product cyanohydrin ester from the aqueous reaction mass comprises adding water and a water immiscible solvent, such as methylene chloride, to the reaction mass and stirring for a time sufficient for the water-immiscible solvent to extract the cyanohydrin ester from the reaction mass; and then separating the water immiscible solvent from the reaction mass, and subsequently, the cyanohydrin ester from the water immiscible solvent, as for example, by evaporating the solvent to leave the ester.

Conversion generally ranges from about 60% to 100%.

When conducting the reaction in a two-phase media a mixture of the carboxylic acid anhydride and a phase transfer catalyst is prepared in an inert water-immiscible solvent, and this mixture is then brought into contact with an aqueous solution of the alkali metal cyanide and alkali metal borohydride at a temperature and for a time sufficient to form the cyanohydrin ester.

There are many water-immiscible solvents known in the art in which the carboxylic acid anhydrides are soluble and which can be used in the practice of the present invention. These include, but are not limited to methylene chloride and other halogenated hydrocarbons; aliphatic hydrocarbons, aromatic hydrocarbons and ether solvents; although methylene chloride is preferred.

The relative amount of water-immiscible solvent used is not critical but it is generally preferred that the mixtures of carboxylic acid anhydride and water-immiscible solvent contain total concentrations of carboxylic acid anhydride ranging from about 5% to about 50% by weight of mixture.

The phase transfer catalysts which are employed in the process of the present invention can be any of those which are generally used for phase-transfer reactions. These include, but are not limited to, quaternary ammonium salts which are soluble in both the aqueous and organic phases, such as benzyl trimethyl ammonium chloride,
tetra-n-butyl ammonium bromide,
tetra-n-butyl ammonium iodide and
tetra-n-hexyl ammonium bromide; although tetra-n-butyl ammonium bromide and tetra-n-butyl ammonium iodide are preferred; with tetra-n-butyl ammonium bromide being most preferred. Other types of phase transfer catalysts may also be used.

The amount of phase transfer catalyst used ranges from about 0.005% to about 1.0% by weight of water-immiscible solvent used; although amounts ranging from about 0.1% to about 0.3% by weight of solvent are preferred.

The mixture of carboxylic acid anhydride, phase transfer catalyst and water-immiscible solvent is prepared using conventional means such as, for example, by bringing the components together and stirring until a uniform mixture is formed.

The aqueous solutions of alkali metal cyanide and alkali metal borohydride employed in the two-phase technique are the same as those described earlier in connection with the use of the aqueous reaction media.

The aqueous alkali metal borohydride/alkali metal cyanide solution and the mixture of carboxylic acid anhydride, phase transfer catalyst and water-immiscible solvent are then brought into contact with each other under such conditions as will promote a phase transfer reaction involving the carboxylic acid anhydride, phase transfer catalyst, alkali metal cyanide and alkali metal borohydride. This can generally be accomplished by intimately mixing the mixture and solution to form a reaction mixture.

Once the reaction mixture is formed, the phase transfer reaction will take place. This reaction is exothermic and external cooling may be required.

The reaction temperature should be maintained below about 50° C. as at temperatures in excess of about 50° C. an alcohol product can result instead of the desired cyanohydrin ester. A preferred temperature range is from about 20° C. to about 40° C.

The essential completion of the reaction will be indicated by the disappearance of the characteristic anhydride absorption bands in the infrared spectrum. The conversion of the carboxylic acid anhydride to cyanohydrin ester will range from about 60 percent to about 100 percent.

The water-immiscible phase is then separated from the reaction mixture, and the solvent evaporated to yield the cyanohydrin ester product.

In a particularly preferred embodiment, the present invention comprises a method for preparing R, S,-α-cyano-3-phenoxybenzyl-(cis, trans)-3-2,2-dimethyl cyclopropane carboxylate which comprises bringing a solution of 3-phenoxybenzoic dichlorochrysanthemic anhydride in a water miscible solvent into contact with an aqueous solution of an alkali metal cyanide and an alkali metal borohydride, and maintaining the contact for a period of time sufficient to convert at least a portion of the 3-phenoxybenzoic dichlorochrysanthemic anhydride to R, S-α-cyano-3-phenoxybenzyl-(cis, trans)-3-(2,2-dichlorovinyl)-2,2-dimethyl cyclopropane carboxylate.

In another particularly preferred embodiment, the present invention comprises a process for preparing R, S-α-cyano-3-phenoxybenzyl(cis, trans)-3(2,2-dichlorovinyl)-2,2-dimethyl cyclopropane carboxylate which comprises reacting 3-phenoxybenzoic dichlorochrysanthemic anhydride with sodium cyanide and sodium borohydride by a phase transfer reaction in the presence of a phase transfer catalyst.

In order that the present invention be more fully understood, the following examples are given by way of illustration, no specific details or enumerations contained therein should be construed as limitations except insofar as they appear in the appended claims. All parts and percentages are by weight unless otherwise specifically designated.

EXAMPLE 1

Preparation of Benzaldehyde Cyanohydrin Benzoate

A solution of 4.0 g (0.082 moles) of sodium cyanide and 0.50 (0.013 moles) of sodium borohydride in 25 milliliters of water was prepared in a flask equipped with a magnetic stirrer. To the flask was then added a solution of 10.0 grams (0.044 mole) of benzoic anhydride in 150 milliliters of dioxane. The flask contents were stirred for twenty minutes after which water and methylene chloride were added. Stirring continued for about 5 minutes after which the flask contents were permitted to settle into two phases. The organic phase was removed, washed with water and concentrated on a rotary evaporator to yield 5.1 grams (98% theory) of a yellow liquid which was determined to be cyanohydrin ester by infrared analysis, ir$\nu_{c=o}$1735 cm$^{-1}$.

EXAMPLE 2

Preparation of R,S-α-Cyano-3-Phenoxybenzyl (Cis, Trans)-3-(2,2-Dichlorovinyl)-2,2-Dimethyl Cyclopropane Carboxylate Using conventional techniques, 3-phenoxybenzoic dichlorochrysanthemic anhydride was prepared from 3-phenoxybenzoyl chloride and dichlorochrysanthemic acid.

A solution of 1.1 gram (0.022 mole) of sodium cyanide and 0.10 grams (0.0026 mole) of sodium borohydride in 5 milliliters of water was then prepared in a flask equipped with a magnetic stirrer. To this was added a solution of 4.07 grams (0.010 mole) of the 3-phenoxybenzoic dichlorochrysanthemic anhydride in 15 milliliters of dioxane. The temperature of the flask contents rose from the initial ambient temperature to 39° C. very quickly. Stirring continued for a total time of about 30 minutes, after which the cyanohydrin ester product was recovered by the same procedure described in Example 1. The final product, which was an orange oil, was identified as a cyanohydrin ester by infrared analysis and further identified as the desired R,S-α-cyano-3-phenoxybenzyl-(cis, trans)-3-(2,2-dichlorovinyl)-2,2-dimethyl cyclopropane carboxylate by infrared and TLC analysis against an authentic sample of that compound.

EXAMPLE 3

Preparation of R,S-α-Cyano-3-Phenoxybenzyl (Cis, Trans)-3-(2,2-Dichlorovinyl)-2,2-Dimethylcyclopropane Carboxylate A solution of 1.0 gram (2.46 m moles) of m-phenoxybenzoic dichlorochrysanthemic anhydride and 0.030 gram of tetra-n-butyl ammonium bromide in 12 milliliters of methylene chloride was prepared in a flask equipped with a magnetic stirrer. A solution of 0.25 grams (5.1 m moles) of sodium cyanide and 0.030 grams (0.79 m moles) of sodium borohydride in 1 milliliter of water was then added to the flask. Stirring was continued under ambient conditions for one hour, after which the organic layer was removed and dried over MgSO4. Filtration and evaporation of the organic layer provided 0.26 grams of the expected product, which was confirmed to be a cyanohydrin ester by infrared analysis, ir$\nu_{c=o}$1735 cm$^{-1}$.

It will thus be seen that the process of the present invention enables the preparation of cyanohydrin esters by a one-step process which does not require the use of free cyanohydrins.

The objects set forth above, among those made apparent from the preceding description are, therefore effectively attained and, since certain changes may be made in the above method without departure from the scope of the invention, it is intended that all matter contained in the above description shall be interpreted as illustrative and not in a limiting sense.

What is claimed is:

1. A process for preparing cyanohydrin esters represented by the formula

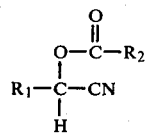

wherein $R^1$ and $R^2$ may be the same or different and each represents an alkyl, alkenyl, cycloalkyl, aryl, aralkyl, alkylphenyl ether or polyphenyl radical, or a radical made up of any combination thereof; and may contain an inert substituent selected from the group consisting of halogen, alkyl and alkoxy; said radical having a total number of carbon atoms ranging from 1 to about 30; which comprises reacting a carboxylic acid anhydride represented by the structure

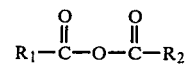

wherein $R_1$ and $R_2$ have the aforedescribed meaning, with an alkali metal cyanide and an alkali metal borohydride.

2. The process of claim 1 wherein said carboxylic acid anhydride is selected from the group consisting of benzoic anhydride, butyric anhydride, 4-chloro-α-isopropyl phenylacetic 3-phenoxybenzoic anhydride, 3-phenoxybenzoic chrysanthemic anhydride and 3-phenoxybenzoic dichlorochrysanthemic anhydride.

3. The process of claim 2 wherein said alkali metal cyanide is selected from the group consisting of sodium cyanide, potassium cyanide and lithium cyanide.

4. The process of claim 3 wherein said alkali metal borohydride is selected from the group consisting of sodium borohydride, potassium borohydride and lithium borohydride.

5. The process of claim 1 wherein said reaction is conducted by forming a mixture of said carboxylic acid anhydride and a phase transfer catalyst in a water-immiscible solvent, bringing said mixture into contact with an aqueous solution of an alkali metal borohydride and an alkali metal cyanide and maintaining said contact at a temperature and for a time sufficient to form a cyanohydrin ester.

6. The process of claim 5 wherein said phase transfer catalyst is selected from the group consisting of
benzyl trimethyl ammonium chloride,
tetra-n-butyl ammonium bromide,
tetra-n-butyl ammonium iodide and
tetra-n-hexyl ammonium bromide 7. The process of claim 6 wherein said water-immiscible solvent is methylene chloride.

8. A process for preparing R, S-α-cyano-3-phenoxybenzyl (cis, trans)-3-(2,2-dichlorovinyl)-2,2-dimethyl cyclopropane carboxylate which comprises reacting 3-phenoxybenzoic dichlorochrysanthemic anhydride with sodium cyanide and sodium borohydride by a phase transfer reaction in the presence of a phase transfer catalyst.

9. The process of claim 1 wherein the reaction is conducted by mixing a solution of said carboxylic acid anhydride in a water miscible solvent with an aqueous solution of said alkali metal cyanide and alkali metal borohydride.

10. The process of claim 9 wherein said water miscible solvent is a solvent selected from the group consisting of tetrahydrofuran, dimethoxyethane, bis-(2-methoxyethyl) ether, bis (2-ethoxyethyl) ether and dioxane.

11. A process for preparing R, S-α-cyano-3-phenoxybenzyl-(cis, trans)-3-(2,2-dichlorovinyl)-2,2-dimethyl cyclopropane carboxylate which comprises bringing a solution of 3-phenoxybenzoic dichlorochrysanthemic anhydride in a water miscible solvent into contact with an aqueous solution of an alkali metal cyanide and an alkali metal borohydride and maintaining the contact for a period of time sufficient to convert at least a portion of the 3-phenoxybenzoic dichlorochrysanthemic anhydride to R, S-α-cyano-3-phenoxybenzyl-(cis, trans)-3-(2,2-dichlorovinyl)-2,2-dimethyl cyclopropane carboxylate.

* * * * *

UNITED STATES PATENT AND TRADEMARK OFFICE
CERTIFICATE OF CORRECTION

PATENT NO. : 4,234,508
DATED : Nov. 18, 1980
INVENTOR(S) : James M. Photis

It is certified that error appears in the above-identified patent and that said Letters Patent are hereby corrected as shown below:

Col. 7, line 63 - "alkylphenyl ether" should be

-- alkylphenyl, diphenyl ether --.

Signed and Sealed this

Twenty-fourth Day of February 1981

[SEAL]

Attest:

RENE D. TEGTMEYER

Attesting Officer

Acting Commissioner of Patents and Trademarks